US010315296B2

(12) United States Patent
Victor et al.

(10) Patent No.: US 10,315,296 B2
(45) Date of Patent: Jun. 11, 2019

(54) TORQUE LIMITER HAVING A LOBED SHAPED MECHANISM

(71) Applicant: Greatbatch Ltd., Clarence, NY (US)

(72) Inventors: Gary C. Victor, Wheatfield, NY (US); Kari Ann Sausen, Clarence, NY (US); Neal N. Nesselbeck, Lockport, NY (US)

(73) Assignee: VIANT AS&O HOLDINGS, LLC, Tempe, AZ (US)

( * ) Notice: Subject to any disclaimer, the term of this patent is extended or adjusted under 35 U.S.C. 154(b) by 314 days.

(21) Appl. No.: 15/168,271

(22) Filed: May 31, 2016

(65) Prior Publication Data

US 2016/0346909 A1    Dec. 1, 2016

Related U.S. Application Data

(60) Provisional application No. 62/168,084, filed on May 29, 2015.

(51) Int. Cl.
*B25B 23/14* (2006.01)
*A61B 17/16* (2006.01)
(Continued)

(52) U.S. Cl.
CPC .......... *B25B 23/141* (2013.01); *A61B 17/162* (2013.01); *A61B 90/03* (2016.02);
(Continued)

(58) Field of Classification Search
CPC ... B25B 23/141; B25B 23/147; B25B 21/002; A61B 90/03; A61B 17/16; A61B 17/162;
(Continued)

(56) References Cited

U.S. PATENT DOCUMENTS 2,775,326 A * 12/1956 Better .................. B25B 23/141
192/56.5
2,973,848 A * 3/1961 Dixon .................. B23P 19/065
192/47
(Continued)

FOREIGN PATENT DOCUMENTS

WO    2013138336    9/2013
WO    2015109191    7/2015

OTHER PUBLICATIONS

Extended European Search, Application 16171911.7, dated Oct. 27, 2016.

*Primary Examiner* — David B. Thomas
(74) *Attorney, Agent, or Firm* — Grossman, Tucker, Perrault & Pfleger, PLLC

(57) ABSTRACT

A torque limiting tool is described. The tool comprises a torque limiting mechanism comprising a sleeve connectable to a drive shaft and a torque drive coupler that resides within a housing. The sleeve comprises a sleeve annular sidewall having a plurality of outwardly projecting elongated first lobes and recessed first grooves that are circumferentially positioned along the length thereof. The drive coupler comprises a socket defined by a coupler annular sidewall having a plurality of outwardly projecting second elongated lobes and recessed second grooves positioned along the coupler interior sidewall. Torque is transferred therebetween when the ramped surfaces of the first and second lobes mate within respective second and first grooves of the coupler and sleeve. When a torque limit is exceeded, the first and second lobes of the sleeve and coupler disengage for their respective second and first grooves.

23 Claims, 12 Drawing Sheets

(51) Int. Cl.
- *B25B 21/00* (2006.01)
- *B25B 23/147* (2006.01)
- *F16D 43/202* (2006.01)
- *A61B 90/00* (2016.01)
- *F16D 7/04* (2006.01)
- *F16D 7/00* (2006.01)
- *A61B 17/88* (2006.01)

(52) U.S. Cl.
CPC .......... *B25B 21/002* (2013.01); *B25B 23/147* (2013.01); *F16D 7/002* (2013.01); *F16D 7/048* (2013.01); *F16D 43/2028* (2013.01); *A61B 17/16* (2013.01); *A61B 17/1626* (2013.01); *A61B 17/8875* (2013.01); *A61B 2090/031* (2016.02)

(58) Field of Classification Search
CPC ............ A61B 17/1626; A61B 17/8875; A61B 2090/031; F16D 7/002; F16D 7/048; F16D 43/2028

See application file for complete search history.

(56) References Cited

U.S. PATENT DOCUMENTS

| | | | |
|---|---|---|---|
| 2,978,082 A * | 4/1961 | Better | B25B 23/141 192/56.5 |
| 3,695,059 A | 10/1972 | Laubach | |
| 4,063,474 A | 12/1977 | Klopping | |
| 5,242,154 A * | 9/1993 | Schmidt | B62D 43/045 254/323 |
| 5,601,491 A * | 2/1997 | Chan | F16D 7/048 192/56.1 |
| 5,746,298 A | 5/1998 | Krivec et al. | |
| 6,439,086 B1 * | 8/2002 | Bahr | B25B 23/141 81/467 |
| 6,487,943 B1 | 12/2002 | Jansson et al. | |
| 7,025,151 B2 | 4/2006 | Hehli et al. | |
| 7,197,968 B2 | 4/2007 | Bubel | |
| 7,334,509 B1 | 2/2008 | Gao | |
| 7,475,619 B2 | 1/2009 | Chiu et al. | |
| 7,762,164 B2 | 7/2010 | Nino et al. | |
| 7,938,046 B2 | 5/2011 | Nino et al. | |
| 8,136,431 B2 * | 3/2012 | Wengreen | A61B 17/8875 81/467 |
| 8,276,487 B2 * | 10/2012 | Wengreen | A61B 17/8875 81/467 |
| 8,549,963 B2 | 10/2013 | Chuang | |
| 8,757,035 B2 | 6/2014 | Kerboul et al. | |
| 8,833,211 B2 | 9/2014 | Chuang | |
| 8,875,602 B2 * | 11/2014 | Wengreen | A61B 17/8875 81/467 |
| 9,097,311 B2 * | 8/2015 | Fujisawa | F16H 35/10 |
| 9,504,528 B2 * | 11/2016 | Ivinson | B25B 23/141 |
| 9,695,882 B2 * | 7/2017 | Jakoubek | F16D 7/048 |
| 2004/0077409 A1 * | 4/2004 | Lattuca | F16D 7/048 464/37 |
| 2008/0178714 A1 * | 7/2008 | Gross | B25B 23/141 81/473 |
| 2008/0188315 A1 * | 8/2008 | Bosserdet | F16D 7/048 464/30 |
| 2010/0179560 A1 * | 7/2010 | Chenaux | A61B 17/8875 606/104 |
| 2010/0275746 A1 | 11/2010 | Wengreen | |
| 2011/0009198 A1 * | 1/2011 | Yang | F16D 7/002 464/46 |
| 2013/0237328 A1 * | 9/2013 | Billings | F16D 7/002 464/37 |
| 2014/0157926 A1 | 6/2014 | Fujisawa et al. | |
| 2015/0252855 A1 * | 9/2015 | Jakoubek | F16D 7/048 464/37 |
| 2017/0105813 A1 * | 4/2017 | Rash | A61B 17/8875 |

* cited by examiner

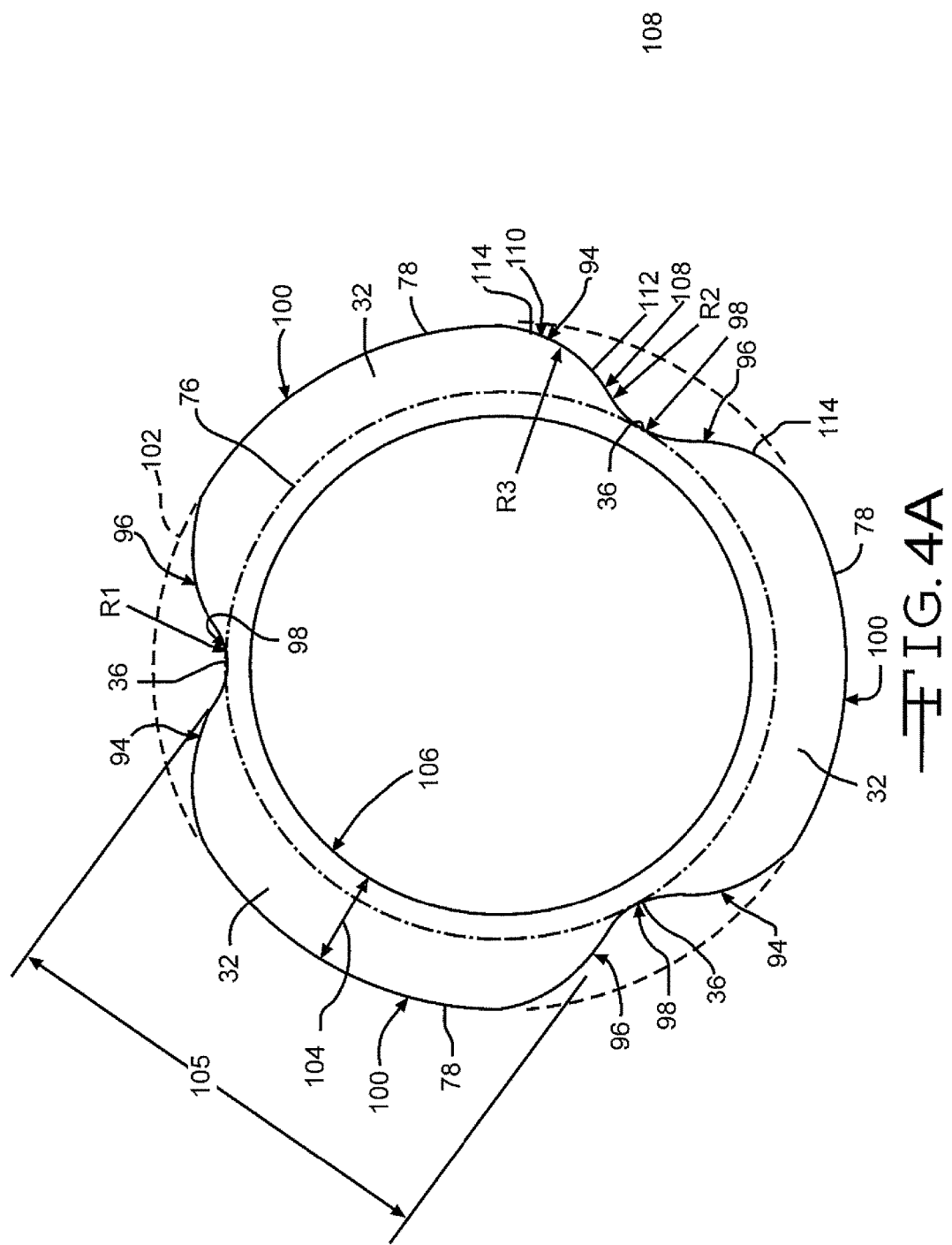

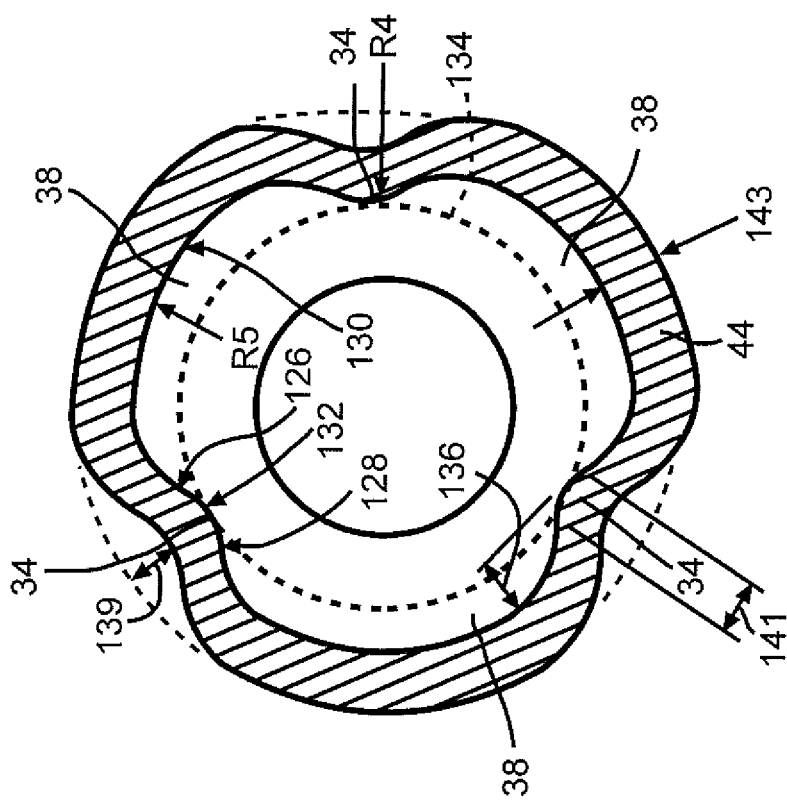

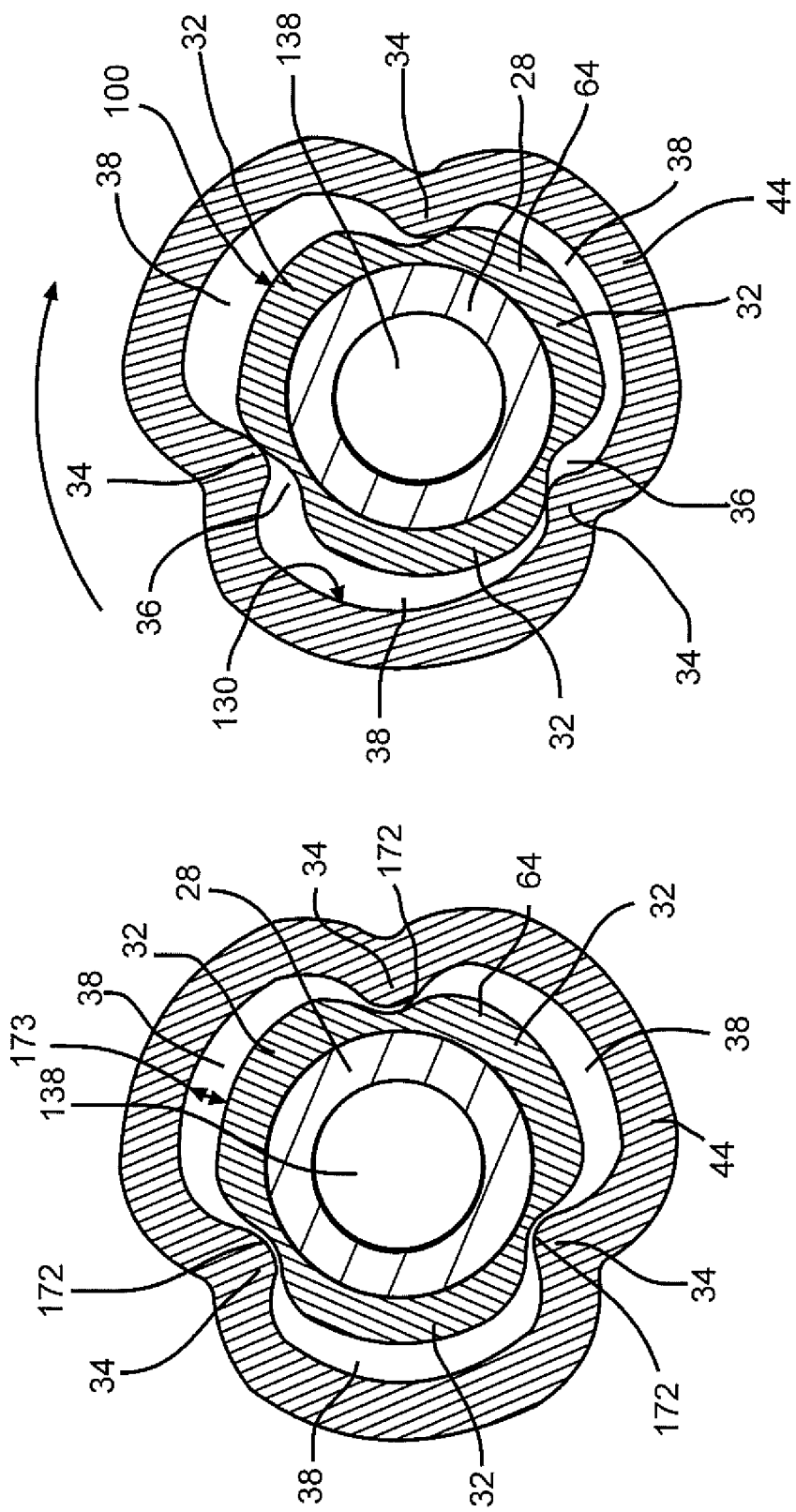

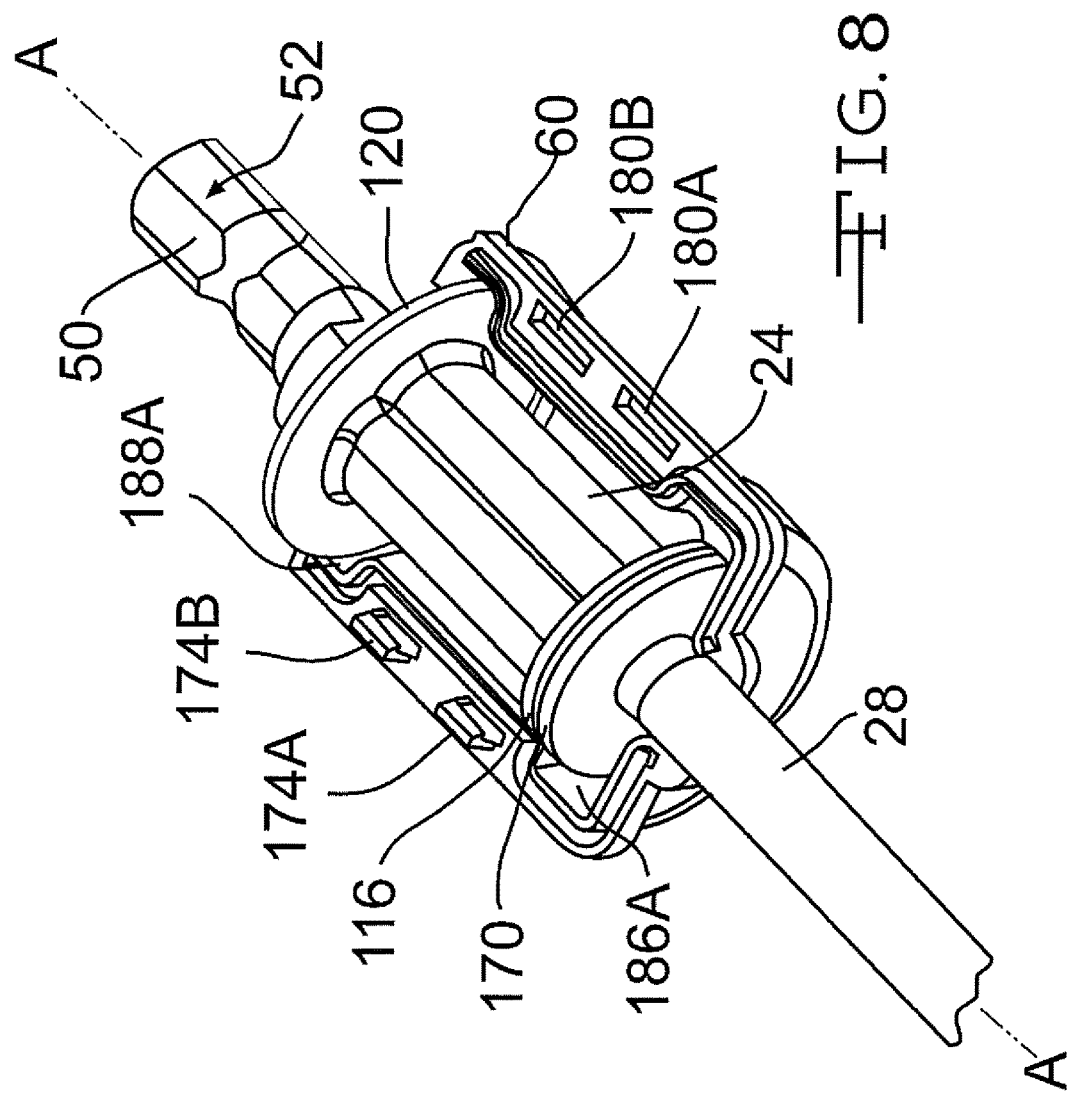

TORQUE LIMITER HAVING A LOBED SHAPED MECHANISM

CROSS REFERENCE TO RELATED APPLICATION

This application claims priority from U.S. Provisional Application Ser. No. 62/168,084, filed May 29, 2015.

TECHNICAL FIELD

This invention relates to the art of instruments used in orthopedic surgical procedures. More specifically, this invention relates to a torque limiting tool that is used to limit the amount of torque applied to a fastener or cutting tool during an orthopedic surgical reaming procedure.

BACKGROUND OF THE INVENTION

Torque limiting tools are widely used to tighten a fastener to a specific torque. Such tools are extensively used during surgical procedures, such as an orthopedic surgical procedure. For example, a torque limiting tool may be used to tighten a fastener that is used to secure an orthopedic implant or bone plate. As such, it is often important that the fastener is tightened to a specific torque. Over-tightening a fastener could result in damage to the orthopedic implant or bone plate. Likewise, a fastener that is not adequately tightened may result in undesirable movement of the implant or bone plate within the patient. Such movement of the orthopedic implant or bone plate may be adverse to a patient as the implant may move to a position that does not allow proper bone repair.

In addition, torque limiting tools may also be used to control the amount of torque that is applied during an orthopedic surgical procedure, such as the reaming of a bone. One such procedure is the reaming of the intramedullary canal of a long bone, such as a femur. During the procedure, a cutting tool that is positioned at the end of a shaft is inserted within the intramedullary canal. Torque applied to the shaft rotates the cutting tool so that tissue and bone material are removed from the canal. It is important that an appropriate amount of torque is applied to the shaft during this reaming procedure to ensure that the canal is appropriately reamed. Application of an excessive amount of torque, however, may adversely result in damage to the shaft or the canal. Therefore, it is important that the amount of applied torque is limited to minimize the possibility of causing injury to the patient.

Prior art torque limiters are generally constructed having a complex structure typically comprising a plurality of bias members and ball bearings. During use, the various forces that are applied to these tools generally cause wear of their components which may result in the tool becoming misaligned. As a result, many of the prior art torque limiters require maintenance and calibration. In contrast, the torque limiting device of the present invention comprises two components: a torque drive coupler that mates with a sleeve that is connectable to a drive shaft. Because the torque limiter of the present invention comprises fewer components than prior art devices, the torque limiting device of the present invention is less likely to become misaligned and thus require re-calibration. In addition, the fewer number of components that comprise the torque limiting device of the present invention makes the device more conducive to manufacture.

More specifically, the tool and the torque limiting mechanism of the present invention comprises a sleeve having a plurality of longitudinally extending first lobes that outwardly project from the annular sidewall of the sleeve. A first groove is positioned longitudinally between two adjacent first lobes. A drive shaft is positionable within at least a portion of a throughbore that extends through the sleeve. The drive coupler comprises a socket defined by an annular coupler sidewall within which the sleeve is received. A plurality of longitudinally extending second lobes outwardly project from an interior surface of the annular sidewall within the coupler socket. In addition, a second groove is positioned longitudinally between two adjacent second lobes.

The sleeve and the coupler socket are configured so that they mate together. The plurality of first and second elongated lobes of the sleeve and coupler socket are received within a corresponding first and second grooves of the sleeve and coupler socket. Rotation of the coupler causes a physical interference of the mated lobes of the sleeve and coupler socket that results in torque being transferred from the coupler to the sleeve and connected drive shaft. When the magnitude of torque applied to the coupler exceeds a torque limit, the coupler and sleeve become disengaged. The respective first and second lobes of the sleeve and coupler socket ride out of their corresponding second and first grooves when a torque limit is exceeded.

SUMMARY OF THE INVENTION

The present invention provides a torque limiting tool and mechanism thereof that is designed to limit the application of torque at a specific magnitude threshold. More specifically, the torque limiting tool of the present invention is configured to limit the maximum amount of torque that is capable of being applied in either a clockwise or counter-clockwise direction. The torque limit of the present invention can be used to tighten a fastener, such as a fastener used to secure an orthopedic implant or bone plate, or alternatively, to limit the amount of torque that is applied during an orthopedic surgical reaming procedure.

The tool of the present invention comprises a sleeve that is connectable to a drive shaft that engages within a torque drive coupler. The sleeve is constructed having a plurality of elongated first lobes that are circumferentially positioned along the length of the sleeve. Each of the first lobes outwardly project from the exterior of the sleeve. In addition, an elongated first groove is positioned extending longitudinally between two adjacent first lobes such that a plurality of alternating first lobes and grooves are circumferentially positioned about the exterior of the sleeve.

The drive coupler comprises a socket, defined by a coupler annular sidewall, within which a plurality of second elongated lobes are positioned extending longitudinally along the interior coupler socket sidewall surface. The plurality of elongated second lobes are positioned circumferentially about the socket interior sidewall. Each of the second lobes outwardly project from the interior of the socket sidewall towards the socket interior. In addition, an elongated second groove extends longitudinally between two adjacent second lobes such that a plurality of alternating second lobes and grooves are positioned circumferentially about the coupler socket interior sidewall.

Torque is transferred when the first and second lobes of the sleeve and torque transfer coupler are engaged and mated with respective second and first elongated grooves of the coupler socket and sleeve. The applied torque rotates the coupler which causes the mated sleeve to rotate therewithin. Continued application of torque in excess of the torque limit threshold causes the first and second lobes of the sleeve and coupler socket to ride out of their respective grooves. The torque limiting mechanism of the present invention can be used in either a clockwise or counterclockwise direction.

In addition, the amount of torque imparted by the tool to a fastened or cutting tool is influenced by the material of which the sleeve and coupler are constructed. Material selection can have a direct effect on the flexural movement of the lobes and respective groove surfaces of the sleeve and coupler as different materials have differing mechanical properties. For example, materials having an increased modulus of elasticity tend to exhibit a greater mechanical stiffness, thereby requiring the application of a greater force to bend or flex the material. Therefore, constructing the sleeve and coupler of a material having a greater modulus of elasticity requires the application of an increased amount of force to flex and separate the respective sleeve and coupler, thus increasing the amount of torque imparted by the tool. These and other additional unique structural features of the torque limiting tool will be discussed in further detail.

BRIEF DESCRIPTION OF THE DRAWINGS

FIG. 4A is a magnified end view of the sleeve shown in FIG. 4 taken from the sleeve proximal end.

FIG. 5A is a cross sectional view of an embodiment of the coupler socket taken perpendicular to longitudinal axis A-A.

FIGS. 7A-7C show cross sectional views of the sleeve engaged within the coupler of the torque limiting mechanism of the present invention as the coupler is rotated in a clockwise direction.

FIG. 8 is a perspective view of an assembled mechanism positioned within a first housing section.

DETAILED DESCRIPTION OF THE PREFERRED EMBODIMENT

Figure 1:
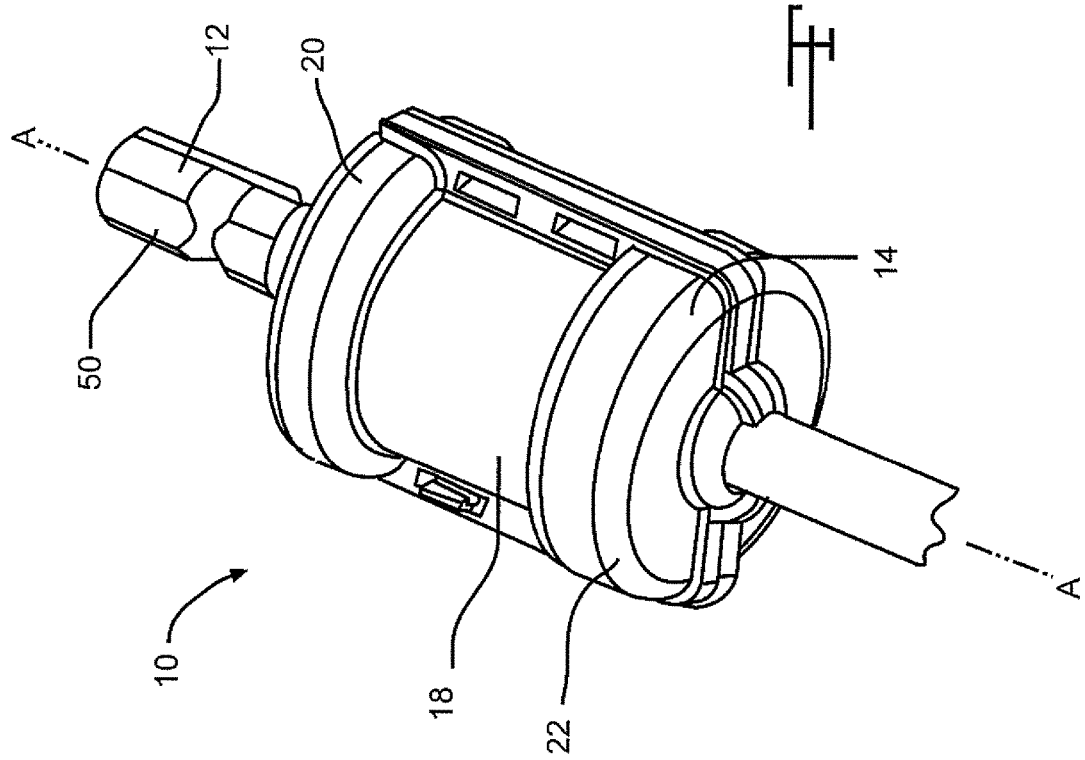
FIG. 1 illustrates a perspective view of an embodiment of the torque limiting tool of the present invention.

Now turning to the figures, FIGS. 1-3 and 8 illustrate a preferred embodiment of a torque limiting tool 10 of the present invention. As shown, the tool 10 extends along longitudinal axis A-A from a proximal end 12 to a distal end 14. In an embodiment illustrated in FIG. 2, the tool 10 comprises a torque limiting mechanism 16 that resides within a housing 18 having a proximal housing end 20 that extends to a distal housing end 22. The mechanism 16 comprises a torque drive coupler 24 and a sleeve 26 that is connectable to a drive shaft 28. The sleeve 26 is preferably positioned within a socket 30 of the coupler 24 in a mated relationship therebetween. Torque is transferred by rotation of the coupler 24 which causes the sleeve 26 and a connected drive shaft 28 to rotate. It is noted that longitudinal axis A-A serves as the rotational axis for the tool 10.

Figure 2:
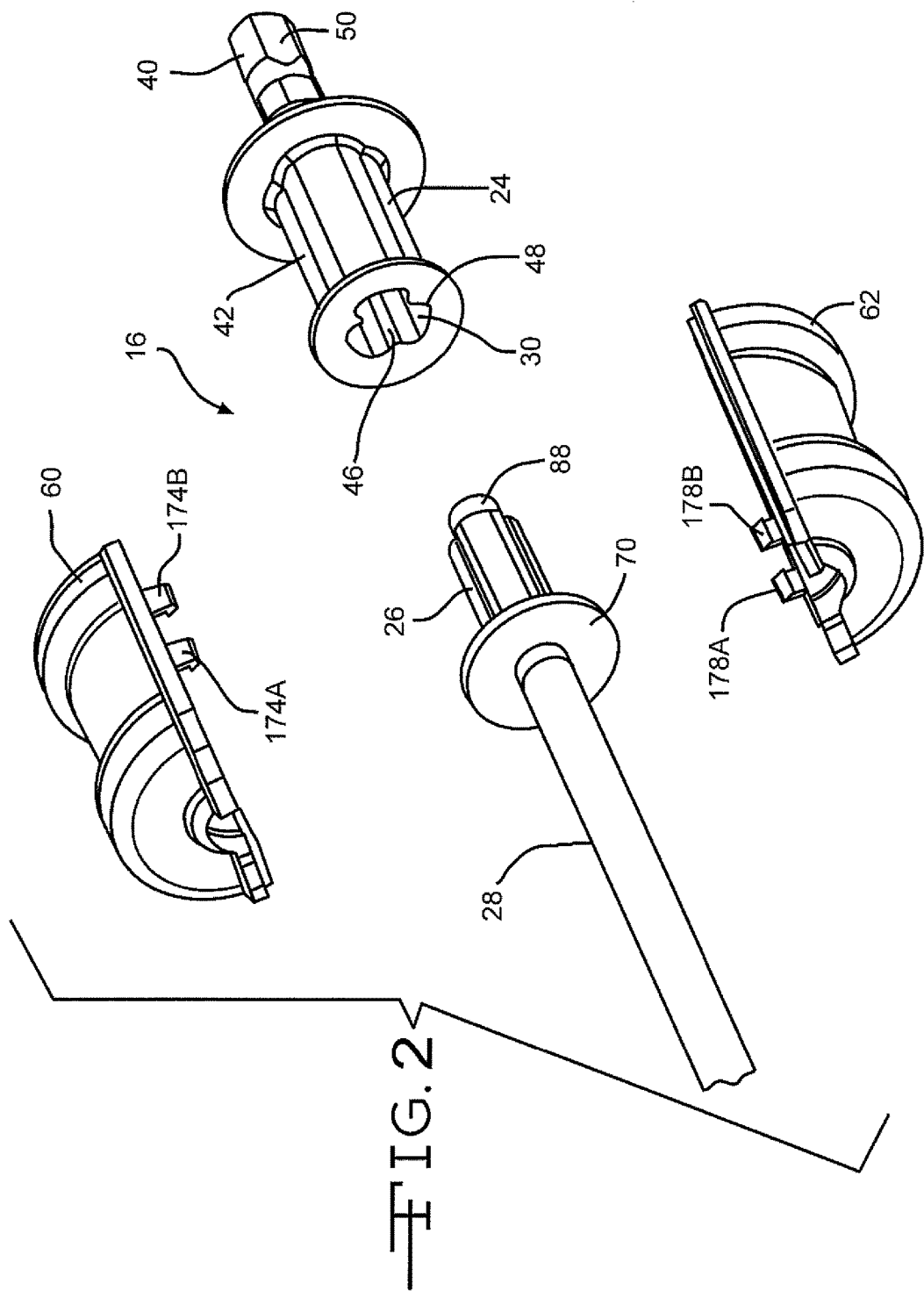
FIG. 2 shows an exploded view of an embodiment of the components that comprise the torque limiting tool of the present invention shown in FIG. 1.
Figure 3:
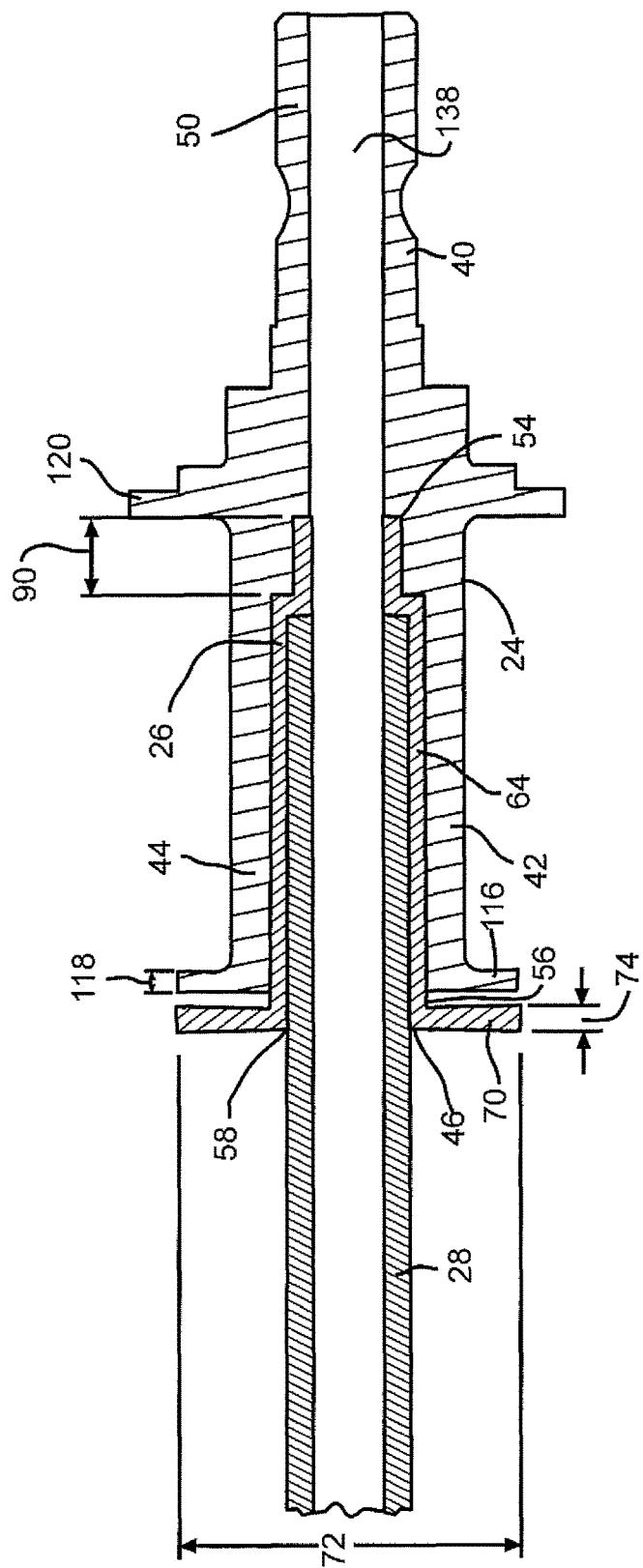
FIG. 3 is a cross-sectional view taken along longitudinal axis A-A of the embodiment of the torque limiting mechanism.

In an embodiment shown in FIGS. 2 and 3, the sleeve 26 and coupler socket 30 of the mechanism 16 comprise a plurality of outwardly projecting first and second elongated lobes 32, 34, respectively, that engage and mate within corresponding first and second grooves 36, 38 of the sleeve 26 and coupler socket 30. In a preferred embodiment, the elongated first lobes 32 of the sleeve 26 mate within the second grooves 38 residing within the coupler socket 30. In addition, elongated second lobes 34 residing within the coupler socket 30 mate within the first grooves 36 of the sleeve 26. Torque is transferred from the coupler 24 to the sleeve 26 when the first and second elongated lobes 32, 34 engage within their respective first and second grooves 36, 38.

FIG. 2 illustrates an exploded view of the torque limiting tool 10 of the present invention and mechanism 16 thereof. As shown, the coupler 24 comprises a coupler proximal portion 40 that extends to a coupler distal portion 42. The coupler socket 30 is defined by a coupler annular sidewall 44 within the distal coupler portion 42. A socket opening 46, within which the sleeve 26 is received, extends through a distal end 48 of the coupler 24. A driver end 50 having a keyed interface 52 comprises the coupler proximal portion 40. The driver end 50 provides a means for the coupler to be connected to an instrument (not shown), such as a drill, that imparts rotation thereto. The sleeve 26 comprises a sleeve proximal end 54 that extends to a sleeve distal end 56. A drive shaft 28 is positionable within an opening 58 that resides at the sleeve distal end 56. The housing 18 preferably comprises a first housing section 60 and a second housing section 62 (FIG. 9) that join together to hold the mechanism 16 therewithin. The housing 18 serves to ensure that the sleeve 26 and the coupler 24 do not come apart, while also allowing for rotation of the sleeve 26 and coupler 24.

As defined herein, torque is a twisting force that tends to cause rotation. More specifically, torque is a measure of a force's tendency to produce rotation about an axis that is equal to the product of the force vector and the radius vector from the axis of rotation to the point of application of the force. Torque has dimensions of force times distance. The International System of Units or SI unit for torque is the Newton meter (Nm). Other non-SI units of torque include pound-force-feet, foot-pounds-force, meter-kilograms-force, inch-ounces, and inch-pounds. As defined herein, a "lobe" is defined as a curved or rounded projection. More specifically, a lobe is a curved elongated rib-like structure that longitudinally extends along and outwardly projects from the sleeve sidewall and coupler socket sidewall, respectively. A "groove" is defined as a curved elongated recess that at least partially extends within the sleeve sidewall and coupler socket sidewall.

Figure 4:
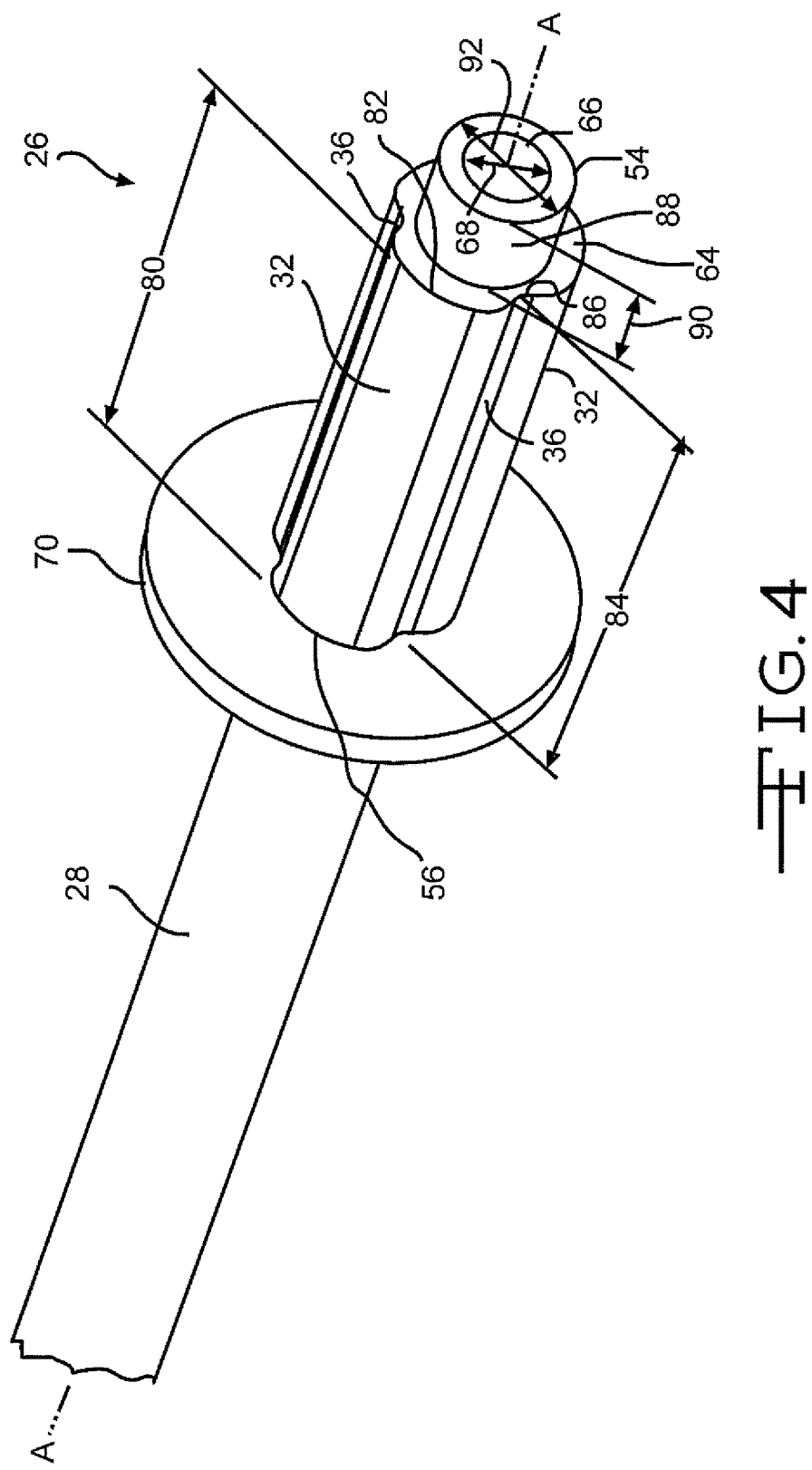
FIG. 4 is a magnified perspective view of an embodiment of the sleeve that is comprised within the torque limiting mechanism of the present invention.

FIGS. 4 and 4A illustrate an embodiment of the sleeve 26 of the present invention. As shown, the sleeve 26 comprises a sleeve annular sidewall 64 that extends from the sleeve proximal end 54 to the sleeve distal end 56. A sleeve throughbore 66, defined by the sleeve annular sidewall 64, extends along longitudinal axis A-A. The sleeve throughbore 66 is preferably dimensioned to allow at least a portion of a drive shaft 28 therewithin. In a preferred embodiment, the sleeve throughbore 66 has a diameter 68 that ranges from about 2 mm to about 10 mm. In addition, the sleeve 26 comprises an end wall 70 that resides at the sleeve distal end 56. In a preferred embodiment, the sleeve end wall 70 is oriented about perpendicular to longitudinal axis A-A with the end wall extending radially outward from the sleeve annular sidewall 64. In a preferred embodiment, the sleeve end wall 70 has a diameter 72 (FIG. 3) intersecting longitudinal axis A-A, which may range from about 0.5 cm to about 5 cm. In addition, the sleeve end wall 70 has a wall thickness 74 that is oriented about parallel to longitudinal axis A-A. In a preferred embodiment the sleeve end wall thickness 74 may range from about 1 mm to about 5 mm.

As previously mentioned, the sleeve 26 comprises a plurality of first lobes 32 and first grooves 36 that are formed by the sleeve annular sidewall 64. As illustrated in FIG. 4, the plurality of first lobes 32 and grooves 36 extend longitudinally from the sleeve distal end 56 towards the sleeve proximal end 54. In addition, the plurality of first lobes 32 and first grooves 36 are positioned circumferentially about the sleeve 26. As shown, a first groove 36 extends lengthwise between two adjacently positioned first lobes 32. In addition, the plurality of first lobes 32 and first grooves 36 are preferably arranged in an alternating manner about the circumference of the sleeve 26, i.e., first lobe, first groove, first lobe.

In a preferred embodiment, each of the plurality of first lobes 32 outwardly projects from the sleeve annular sidewall 64 away from longitudinal axis A-A. As shown, each of the first lobes 32 extends from a first lobe base 76, located proximal to longitudinal axis A-A, to a first lobe plateau 78, located distal of the base 76 and longitudinal axis A-A. In addition, each of the plurality of first grooves 36 are preferably recessed between two adjacently positioned first lobes 32 within the sleeve annular sidewall 64.

In a preferred embodiment illustrated in FIG. 4, each of the first lobes 32 extends lengthwise along a first lobe length 80 from the sleeve end wall 70 at the sleeve distal end 56, to a first lobe proximal end 82 located a distance distal of the sleeve proximal end 54. In addition, each of the first grooves 36 extends lengthwise along a first groove length 84 from the sleeve end wall 70 at the distal sleeve end 56, to a first groove proximal end 86 located a distance distal from the sleeve proximal end 54. In a preferred embodiment, the lengths 80, 84 of each of the first lobes 32 and the first grooves 36 may be about equal. In an embodiment, the lengths 80, 84 of either, or both, of the first lobes 32 and the first grooves 36 may range from about 0.1 cm to about 10 cm. A standoff portion 88 may be constructed at the proximal end 54 of the sleeve 26. In an embodiment, the standoff 88 comprises a portion of the annular sleeve sidewall 64 that extends between the proximal ends 82, 86 of the first lobes 32, grooves 36 and the sleeve end 54. In a preferred embodiment, the standoff portion 88 has a standoff length 90 that may range from about 5 mm to about 10 mm. In addition, the standoff 88 may be constructed having a diameter 92 that is less than the diameter of the sleeve annular sidewall distal portion that comprises the plurality of first lobes and grooves 32, 36. In a preferred embodiment, the standoff diameter 92 may range from about 1 mm to about 8 mm.

FIG. 4A illustrates a cross-sectional view of the sleeve 26 taken perpendicular to longitudinal axis A-A. As shown in the embodiment, there are three, first lobes 32 and three, first grooves 36 that are positioned circumferentially about the sleeve 26 in an alternating fashion, i.e. first lobe, first groove, first lobe, etc. While it is preferred that the sleeve 26 comprise three, first lobes 32 and grooves 36, it is contemplated that the sleeve 26 of the torque limiting mechanism 16 may be constructed having more or a less number of first lobes 32 and respective first grooves 36. In a preferred embodiment, the first lobes 32 and the first grooves 36 are spaced about the circumference of the sleeve 26 at an equal distance and/or angular orientation from each other. For example, in the embodiment comprising three first lobes 32 and grooves 36, the lobes and grooves are spaced about 120° from an adjacent lobe 32 or groove 36, respectively. It is further contemplated that the sleeve 26 may be constructed with at least two first lobes 32 and one first groove 36.

The plurality of alternating first lobes and grooves 32, 36 forms an annular sleeve sidewall 64 having an undulated exterior surface. As shown in FIG. 4A, each of the first lobes 32 and grooves 36 has a curved structure. More specifically, each first groove 32 comprises respective left and right groove surfaces 94, 96 that meet and extend from a groove base surface 98, positioned between two adjacent first lobes 32, to a first lobe plateau surface 100. The respective left and right surfaces 94, 96 of each of the first grooves 36 are preferably formed each having a ramped surface that extends from a ramp base, located at the base 98 of the groove 36, to the plateau surface 100 at the plateau 78 of the first lobe 32. In a preferred embodiment, the left and right groove surfaces 94, 96 of the groove 36 form the first groove 36 having a curved shape. More preferably, the left and right groove surfaces 94, 96 form the first groove 36 having a "U" shape. In a preferred embodiment the groove base surface 98 may be constructed having a first groove radius of curvature $R_1$ that ranges from about 2 mm to about 10 mm.

In a preferred embodiment, the left and right surfaces 94, 96 of the first groove 36 define the respective right and left surfaces of each of the first lobes 32. As illustrated, the left and right surfaces 94, 96 of the groove 36 form the respective right and left surfaces of the first lobe 32 as they are the same. More specifically, the right surface 96 of the first groove 36 forms the left sidewall surface of the first lobe 32 and the left surface 94 of the first groove 36 forms the right sidewall surface of the first lobe 32. As shown, the respective left and right lobe surfaces that extend from the first groove base 98 and meet at the plateau surface 100 of the first lobe 32, define the shape of the first lobes 32. In a preferred embodiment, the left and right lobe surfaces are curved such that the first lobes 32, in particular the cross-section of the first lobes 32, have a curved shape.

In an embodiment, the first lobe plateau surface 100 is curved. More specifically, each of the plateau surfaces 100 of the first lobes 32 is constructed having a concave curvature oriented towards longitudinal axis A-A. This concave curvature of the first lobe 32 enables the lobe 32 to ride up or down the ramped sides of a corresponding second groove 38 of the coupler 24. In a preferred embodiment, the plateau surface 100 of the first lobe 32 is tangent to an imaginary circle 102 having its center positioned along longitudinal axis A-A. Imaginary circle 102 comprises a diameter that ranges from about 1 cm to about 10 cm. In a further embodiment, each of the first lobes 32 has a first lobe thickness 104 that extends outwardly from an inner surface 106 of the sleeve annular sidewall 64. In a preferred embodiment, the thickness 104 of the first lobes 32 may range about 0.05 cm to about 1 cm. In addition, each of the first lobes 32 has a width 105 that spans between the left and right groove surfaces 94, 96. In a preferred embodiment, the first lobe width 105 may range from about 0.5 cm to about 5 cm.

In a preferred embodiment, each of the respective left and right sidewall surfaces 94, 96 of the first groove 32 comprises a compound curvature. As illustrated in FIG. 4A, each of the respective left and right surfaces 94, 96 of the first groove 36 is preferably constructed having a first and second curved transition surfaces 108, 110. In a preferred embodiment, the first transition surface 108 extends from the groove base 98 to a first transition point 112 located along each of the left and right surfaces 94, 96 between the groove base 98 and the plateau surface 100 of the first lobe 32. In an embodiment, the first transition point 112 is located about midway between the groove base 98 and the lobe plateau surface 100. In an embodiment, the first transition surface 108 has a convex curvature with respect to imaginary axis A-A. The first transition surface 108 preferably has a radius of curvature $R_2$ that ranges from about 0.05 cm to about 5 cm. The second transition surface 110 extends from the first transition point 112 to a second transition point 114 located at the end of plateau surface 100. In a preferred embodiment, the second transition surface 110 has a concave radius of curvature with respect to imaginary axis A-A. In addition, the second transition surface 110 preferably has a radius of curvature $R_3$ that ranges from about 0.10 cm to about 5 cm. The compound curvature of the first groove 36 is preferred because it improves the precision of the torque limiting mechanism. More specifically, the compound curvature of the first groove 36 allows for the second lobe 34 of the coupler 24 to ride in and out of the first groove 36 at a more precise amount of torque.

Figure 5:
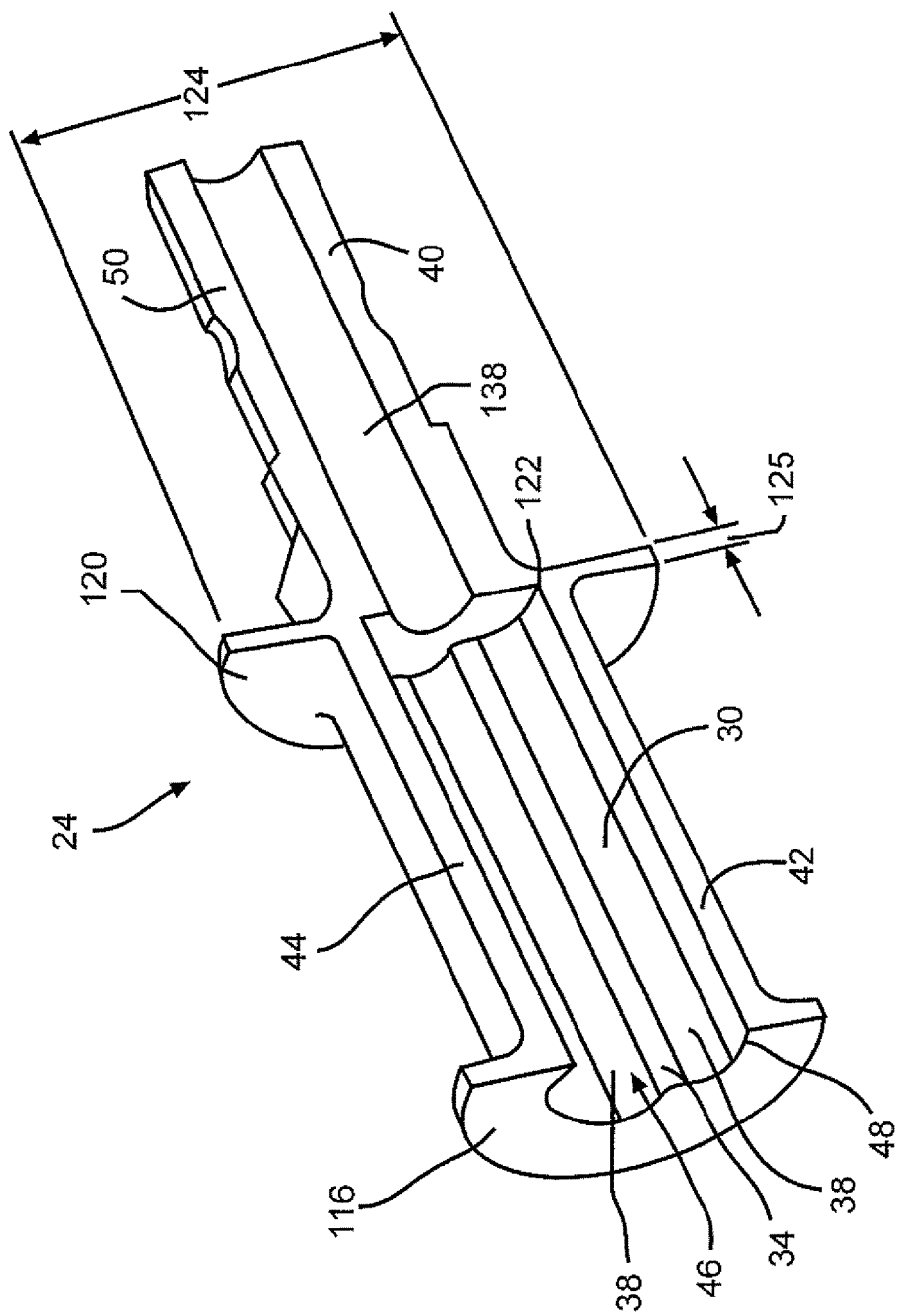
FIG. 5 is a cross sectional view of an embodiment of a drive coupler that is configured within the torque limiting mechanism of the present invention.

FIG. 5 illustrates a cross sectional view of an embodiment of the coupler 24 of the mechanism 16 of the present invention taken along plane intersecting longitudinal axis A-A. As previously mentioned, the coupler 24 comprises a plurality of elongated second lobes 34 that are formed by the annular coupler sidewall 44 that defines the coupler socket 30. Each of the plurality of second lobes 34 extends longitudinally along the annular sidewall 44 and outwardly projects from the sidewall 44 of the coupler socket 30 towards the socket interior and longitudinal axis A-A. In addition, the plurality of second grooves 38 are each formed between two adjacent second lobes 39. In a preferred embodiment, the second groove 38 may be formed so that it is recessed between two adjacently positioned second lobes 34 within the annular coupler sidewall 44 of the socket 30. The mechanism 16 is designed so that the first lobes 32 of the sleeve 26 are mated within respective second grooves 38 of the coupler 24 and the second lobes 34 of the coupler 24 are mated within respective first grooves 36 of the sleeve 26. The first and second elongated lobes 32, 34 of the sleeve 26 and coupler 29, respectively, act similar to that of the teeth of a gear in that torque is transferred between the coupler 24 and the sleeve 26 when the first and second lobes 32, 39 are mated within their respective first and second grooves 36, 38.

In an embodiment, a coupler first end wall 116 is formed at the distal end 48 of the coupler 24. As shown, the first end wall 116 is shaped similar to that of a disc. More preferably, the coupler first end wall 116 is oriented about perpendicular to longitudinal axis A-A extending radially from an external surface of the coupler sidewall 44. In a preferred embodiment, the first end wall 116 has a first end wall diameter intersecting longitudinal axis A-A. The diameter of the first end wall 116 may range from about 0.5 cm to about 5 cm. In addition, the first end wall has a thickness 118 oriented about parallel to longitudinal axis A-A that may range from about 0.1 cm to about 1 cm.

As shown, the socket 30 extends from the socket opening 46 at the distal coupler end 48 through the first end wall 116 to a second coupler end wall 120 that resides at a proximal end 122 of the distal coupler portion 42. In a preferred embodiment, the second coupler end wall 120 is shaped similar to that of a disc. In a preferred embodiment, the second coupler end wall 120 has a second diameter 124 that radially extends perpendicular to longitudinal axis A-A. In a preferred embodiment, the second diameter of the second end wall 120 ranges from about 0.5 cm to about 5 cm. The second end wall has a thickness 125 that extends about parallel to longitudinal axis A-A. In a preferred embodiment, the thickness 125 of the second end wall 120 may range from about 0.1 cm to about 1 cm.

As illustrated in FIGS. 5 and 5A, the plurality of second lobes 34 are formed by the coupler annular sidewall 44 within the coupler socket 30. As shown, each of the second lobes 34 extends lengthwise along longitudinal axis A-A from the distal coupler end 48 to the coupler second end wall 120. Each of the second lobes 34 extends outwardly from the interior surface of the annular coupler sidewall 44 towards longitudinal axis A-A. As shown, the plurality of second grooves 38 extend lengthwise from the distal coupler end 48 to the coupler second end wall 120. In a preferred embodiment, each of the second grooves 38 are positioned between adjacent second lobes 34 such that the interior surface of the annular coupler sidewall within the socket 30 comprises a plurality of second lobes 34 and second grooves 38 in an alternating arrangement.

FIG. 5A illustrates a cross sectional view of the coupler socket 30 taken perpendicular to longitudinal axis A-A. The plurality of alternating second lobes 34 and grooves 38 forms the socket interior having an undulated surface. Each of the second lobes and grooves 34, 38 preferably has a curved structure. In a preferred embodiment, the second lobes 34 are dimensioned to be received within a corresponding first groove 36 of the sleeve 26. As shown, each of the second lobes 34 comprises respective right and left lobe sidewall surfaces 126, 128. In an embodiment, the right and left second lobe sidewall surfaces 126, 128 outwardly extend from respective base surfaces 130 of adjacently positioned second grooves 38 that are partially recessed within the coupler annular sidewall 44. The right and left second lobe surfaces 126, 128 are ramped surfaces that extend from the groove base surface 130 to a second lobe plateau surface 132. More specifically, the respective right and left sidewall surfaces 126, 128 of the second lobe 34 are formed having a ramped surface that extends from the base surface 130 of respective adjacent second grooves 38, positioned left and right of the second lobe 34, towards the second lobe plateau surface 132. In a preferred embodiment, the second lobe plateau surface 132 has a convex curvature with respect to longitudinal axis A-A. In a preferred embodiment, the plateau surface 132 of the second lobe 34 has a radius of curvature $R_4$ that ranges from about 0.5 cm to about 5 cm. The plateau surface 132 of the second lobe 34 comprises a second lobe width 141 that extends between right and left lobe sidewall surfaces 126, 128. In an embodiment the width 141 of the second lobe 34 may be less than the width 105 of the first lobe 32. In a preferred embodiment, the width 141 of the second lobe 34 may range from about 0.1 cm to about 3 cm. In an embodiment, the plateau surfaces 132 of the respective second lobes 34 are tangent to an imaginary circle 134 that originates at longitudinal axis A-A with a diameter that ranges from about 0.5 cm to about 8 cm. In an embodiment, each of the second lobes 34 has a second lobe thickness 136 that extends outwardly from the inner surface of the annular coupler sidewall 44 within the socket 30. In a preferred embodiment, the thickness 136 of the second lobes 34 may range about 0.05 cm to about 1 cm.

In an embodiment, each of the second grooves 38 is dimensioned to receive a corresponding first lobe 32 of the sleeve 26. In an embodiment, each of the second grooves 38 is formed having a "U" shape. More specifically, as illustrated in FIGS. 5 and 5A, the base surface 130 of the second groove 38 extends between respective left and right second groove sidewall surfaces. In a preferred embodiment, the right surface 126 of the second lobe 34 forms the left surface of a second groove 38 that is positioned to the right of the second lobe 34. The left surface 128 of the second lobe 34 forms the right surface of a different second groove 38 that is positioned to the left of the second lobe 34. As illustrated, the base surface 130 of the second grooves 38 has a radius of curvature $R_5$ that ranges from about 1 cm to about 4 cm.

In a preferred embodiment, as illustrated in FIG. 5A, the annular sidewall 44 of the coupler socket 30 is constructed having a uniform thickness 143 about its circumference. This uniform thickness 143 about the circumference of the socket 30 of the coupler 24 enhances flexure of the second lobe 34 is it rides in and out of the first groove 36 of the sleeve 26. In an embodiment, the thickness 143 of the coupler annular sidewall may range from about 2 cm to about 10 cm. In a preferred embodiment, as shown in FIG. 5A, the annular sidewall 44 of the socket 30 comprises an exterior sidewall recess area 139 formed when a portion of the exterior of the sidewall 44, adjacent to the protruding second lobe 34, has been removed. Alternatively, the socket 30 with the sidewall 44 can be a member that is molded with the desired shape. In an embodiment, the exterior recess area 139 extends longitudinally along the length of the coupler socket 30. In a preferred embodiment, the depth of the recess 139 is about the same as the thickness 136 of the second lobe 34. Thus, the exterior sidewall recess area 139 helps ensure a uniform sidewall thickness, particularly in portions of the sidewall 44 that comprise the protruding second lobe 34.

Figure 6:
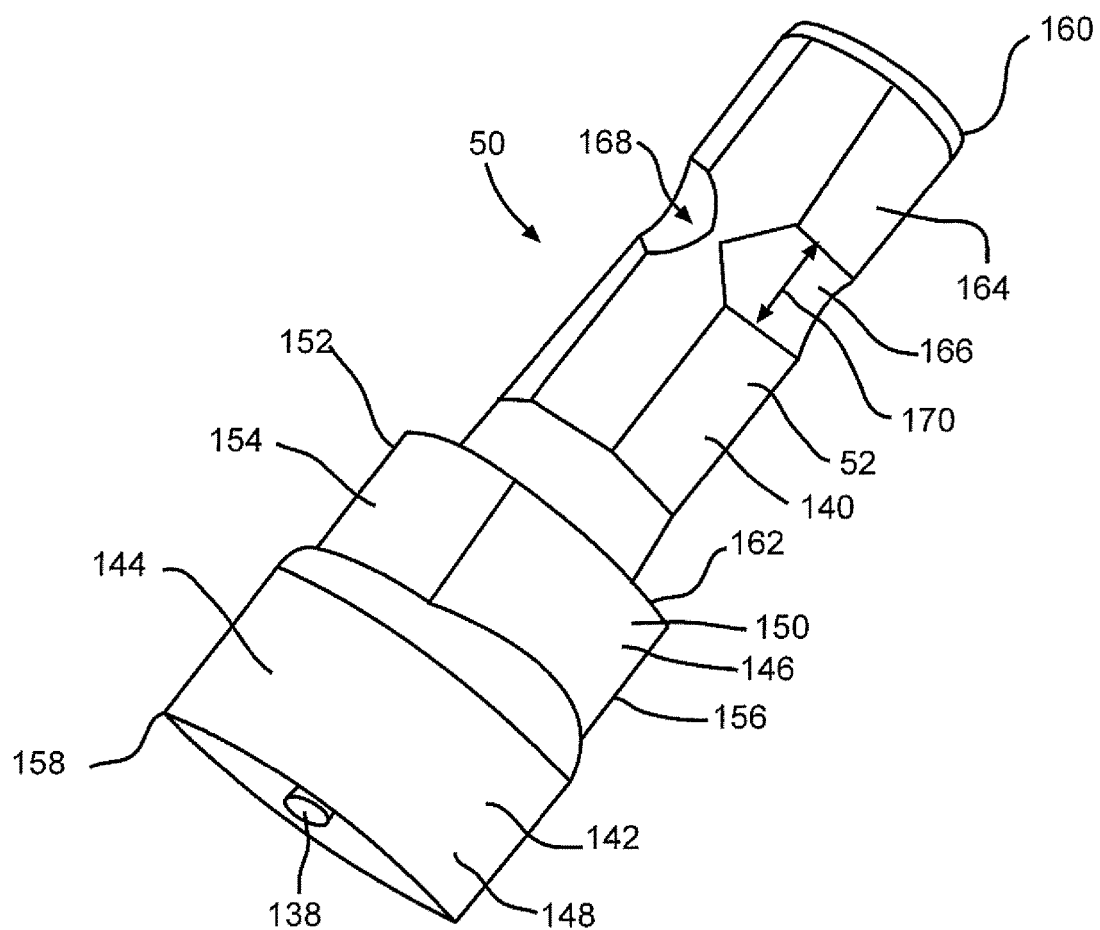
FIG. 6 is a magnified perspective view of the driver end of an embodiment of the coupler.

FIG. 6 illustrates a magnified view of the keyed driver end 50 of the coupler proximal portion 40. In a preferred embodiment, the keyed interface 52 of the driver end 50 may be constructed of a plurality of non-limiting configurations so that it is capable of being removably engaged with a corresponding receptacle of a motor (not shown) having a similar keyed configuration. In a preferred embodiment, the keyed interface 52 may be constructed of a plurality of unlimited geometries, examples of which may include, but are not limited to, a slotted end, a Phillips® end, a Torx® end, a clutch end, or a Pozidriv® end. In addition, the driver end 50 may be constructed having a driver end lumen 138 that extends along longitudinal axis A-A through the length of the driver end 50. The driver end lumen 138 is preferably dimensioned to allow for the passage of a guide wire (not shown). In a preferred embodiment, the lumen 138 is constructed having a lumen diameter that ranges from about 0.1 cm to about 1 cm.

As illustrated in FIGS. 1, 3, 5, and 6, the driver end 50 extends in a proximal direction from the proximal end 122 of the coupler distal portion 42. In a preferred embodiment, the keyed interface 52 of the driver end 50 comprises a shank 140 that extends from a driver end pedestal 142 (FIG. 6) having a first pedestal portion 144 that extends to a second pedestal portion 146. As shown, the first pedestal portion 144 comprises an annular sidewall 148 that outwardly extends from the proximal end 122 of the coupler distal portion 42.

As shown, the second pedestal portion 146 extends in a proximal direction from the first pedestal portion 144. In a preferred embodiment, the second pedestal portion 146 comprises opposed first and second sidewalls 150, 152 that meet and join opposed third and fourth second pedestal sidewalls 154, 156. As illustrated, the opposed first and second sidewalls 150, 152 are positioned about perpendicular to the opposed third and fourth sidewalls 154, 156. In an embodiment, either of the first, second, third or fourth sidewalls 150, 152, 154, and 156 may have a planar or curved sidewall surface.

As illustrated in FIG. 6, the shank 140 extends along longitudinal axis A-A from a distal shank end 158 to a proximal shank end 160 in a proximal direction from a proximal end 162 of the second pedestal portion 146. In an embodiment, the shank 140 may comprise a cross-section of a hexagon geometry that is oriented about perpendicular to longitudinal axis A-A. In the embodiment shown, the shank 140 comprises a cross-section oriented about perpendicular to longitudinal axis A-A having a hexagon shape. As illustrated, the shank 140 is constructed with a plurality of sidewall surfaces 164 that extend lengthwise about longitudinal axis A-A. Each of the sidewall surfaces 164 is preferably planar. Alternatively, the shank 140 may be constructed having a plurality of sidewall surfaces 164 that are curved or combinations of planar and curved surfaces.

In addition, the shank 140 may be constructed having a recess band 166 that extends circumferentially around longitudinal axis A-A. As illustrated, the recess band 166 comprises a recess band surface 168 that at least partially extends within the shank 140. As illustrated, the recess band 166 has a band width 170 that extends parallel to longitudinal axis A-A. In a preferred embodiment, the recess band 166 may be designed having a curved surface 168 that extends inward towards the longitudinal axis A-A. The recess band 166 serves to provide a surface on which a motor or other tool can attach and detach.

Figure 7C:
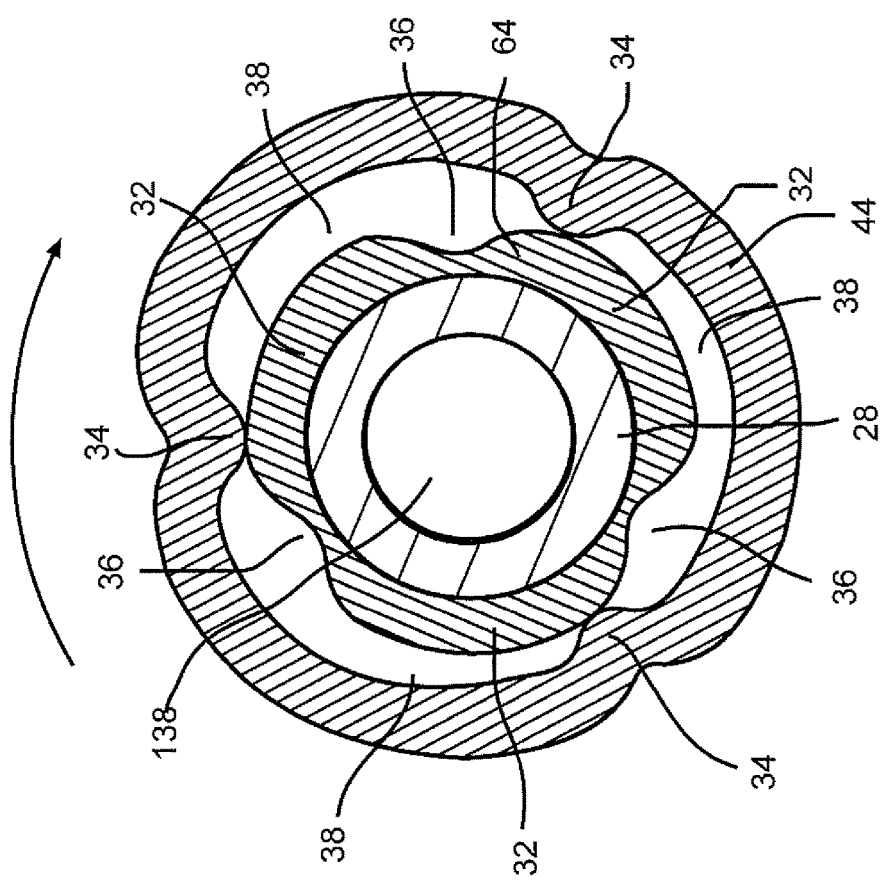

FIGS. 7A-7C illustrate cross sectional views of the mating relationship between the sleeve 26 and the coupler 24 as the coupler 24 is rotated in a clockwise direction. Specifically, FIGS. 7A-7C illustrate cross sectional views taken perpendicular to longitudinal axis A-A of the sleeve 26 positioned within the coupler socket 30. FIG. 7A illustrates the coupler 24 in a fully mated relationship with the sleeve 26. It is in this configuration that torque applied by the coupler 24 is transferred to the sleeve 26 and connected drive shaft 28. As shown, in the embodiment, the second lobes 34 of the coupler socket 30 are engaged within corresponding first grooves 36 of the sleeve 26. In addition, the first lobes 32 of the sleeve 26 are engaged within the second grooves 38 of the coupler 24.

As the coupler 24 is rotated in either a clockwise or counterclockwise direction, torque is being increasingly applied to the sleeve 26 by the coupler 24. More specifically, as the coupler 24 is rotated, an interference is created between the ramped sidewall surface of the second lobe 34 of the coupler 24 and the ramped sidewall surface of the first groove 36 which causes the sleeve 26 and connected drive shaft 28 to rotate in the direction of the coupler 24.

FIG. 7B illustrates an embodiment in which the magnitude of torque applied to the coupler 24 has increased from the embodiment shown in FIG. 7A. As shown, the sidewall surface of the second lobe 34 has partially ridden up the ramped sidewall surface of the first groove 36. In the embodiment, an increased magnitude of torque has been applies to the coupler 24 in a clockwise direction. The plateau surface 132 of the second lobe 34 has started to ride up the ramped right surface 96 of the first groove 36. FIG. 7C illustrates an embodiment in which the second lobes 34 of the coupler 24 are no longer engaged within their respective first grooves 36 of the sleeve 26. In this embodiment, the torque limit has been exceeded as the second lobes 34 of the coupler 24 are shown to be in contact with the plateau surfaces 100 of the first lobes 32 of the sleeve 26.

In an embodiment, a first gap 172 may span between the second lobe 34 of the coupler 24 and first groove 36 of the sleeve 26 as shown in FIG. 7A. This first gap 172 is intended to allow for the movement of the coupler second lobe 34 within a respective first sleeve groove 36. In an embodiment, the torque limit may be adjusted by modifying the first gap 172. In general, decreasing the first gap 172 increases the magnitude of the torque limit while increasing the first gap 172 generally deceases the torque limit magnitude. In a preferred embodiment, the first gap 172 may range from about 0.01 cm to about 0.5 cm. In a preferred embodiment, the sleeve 26 and the torque drive coupler 24 of the mechanism 16 are constructed so that a second gap 173 extends between the plateau surface 100 of the first lobe 32 of the sleeve 26 and the base surface 130 of the second groove 38 of the coupler socket 30. This second gap 173 prevents interference of the first lobe plateau surface 100 with the second groove base surface 130, thus allowing for the coupler 24 to rotate about the sleeve 26.

Figure 9:
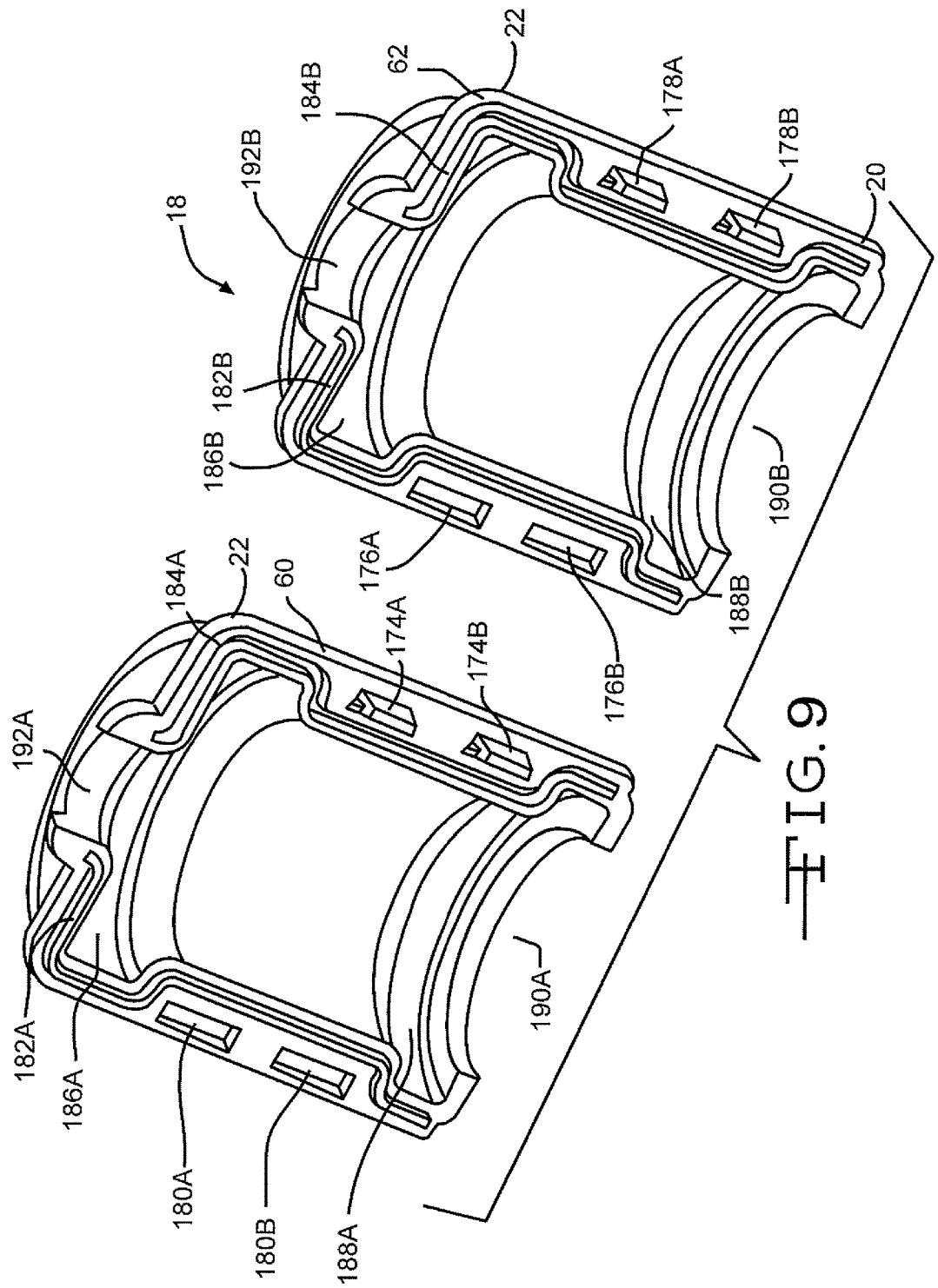
FIG. 9 illustrates a perspective view of an embodiment of the first and second housing sections.

As previously mentioned, the mechanism 16 preferably resides within a housing 18. In an embodiment, shown in FIGS. 8 and 9, the housing comprises a housing first section 60 that connects to a second housing section 62. In an embodiment, the housing sections 60, 62 may be symmetrically constructed so that the first and section housing sections 60, 62 comprise identical top and bottom halves. In a preferred embodiment, the housing 18 may be constructed so that the first and second sections snap together. In an embodiment, the first housing section 60 comprises first prongs 174A, 174B that are received within first openings 176A, 176B of the second housing section 62. The second housing section 62 comprises second prongs 178A, 178B that are received within second openings 180A, 180B that reside within the first housing section 60. In a preferred embodiment, the first and second housing sections 60, 62 are joined together by mating the first and second prongs with their respective openings. In addition, the first and second housing sections 60, 62 may each comprise an alignment ridge 182A, 182B that is received with an alignment groove 184A, 184B of the other of the housing section 60, 62. As illustrated in FIG. 9, the first alignment ridge 182A, positioned along the left side of the first housing section 60, is received within the first alignment groove 184B that resides along the right side of the second housing section 62. In addition, the second alignment ridge 182B, positioned along the left side of the second housing section 62, is received within the second alignment groove 184A positioned along the right side of the first housing section 60. Alternatively, the first and second housing sections 60, 62 may be joined with an adhesive or sealant. In a preferred embodiment, the keyed orientation of the first and second housing prongs and the first and second alignment ridges help ensure proper alignment of the two housing sections 60, 62.

FIG. 8 illustrates an embodiment in which the mechanism 16 is positioned within the first housing section 60. As shown, the first and second housing sections 60, 62 comprise a first well 186A, 186B at the distal housing end 22 and a second well 188A, 188B at the proximal housing end 20. In an embodiment, the first housing well 186A, 186B is configured to receive the sleeve end wall 70 and the first coupler end wall 116 as they are brought together when the sleeve 26 is received within the socket 30 of the coupler 24. As shown, the first well 186A, 186B comprises a first well depth that extends within the housing sidewall at the distal housing end 22. In a preferred embodiment, the housing first well depth is configured to receive the radially dimensioned end walls 70, 116 of the sleeve and coupler 24. In a preferred embodiment, the depth of the first well 186A, 186B may range from about 0.1 cm to about 1 cm. In addition, the first well comprises a first well width that is oriented perpendicular to longitudinal axis A-A. The second well 188A, 188B comprises a second well depth that extends within the housing sidewall at the proximal housing end 20. In a preferred embodiment, the depth of the second housing well 188A, 188B is configured to receive the second end wall 120 of the coupler 24. In a preferred embodiment, the depth of the second housing well 188A, 188B may range from about 0.1 cm to about 1 cm. In addition, the second well comprises a second well width oriented perpendicular to longitudinal axis A-A. In a preferred embodiment, the width of the second housing well ranges from about 0.1 cm to about 1 cm. A first housing opening 190A, 190B is positioned at the housing proximal end 20. The first housing opening 190A, 190B is preferably oriented perpendicular to longitudinal axis A-A and is dimensioned to allow for the drive end 50 of the coupler 24 to extend therethrough. In addition, a second housing opening 192A, 192B may be positioned at the housing distal end 22. In a preferred embodiment, the second housing opening 192A, 192B is configured to allow for the passage of the drive shaft 28.

In an embodiment, the magnitude of the torque limit threshold can be modified by adjusting the number of first and second lobes 32, 34 and respective first and second grooves 36, 38 within which the first and second lobes 32, 34 are received. In addition, the magnitude of the torque limit threshold can be adjusted by modifying the radius of curvatures of the first and second transition surfaces 108, 110 of the sleeve 26. In general, the magnitude of the torque limit threshold can be increased by increasing the number of first and second lobes 32, 34. The increased number of lobes 32, 34 typically increases surface friction between the sleeve 26 and coupler 24, which results in an increase in the torque limit magnitude. In addition, the torque limit magnitude may be increased by decreasing the radius of curvature of the first and second transition surfaces 108, 110. Decreasing the radius of curvature of the first and second transition surfaces 108, 110 of the first lobe 32 generally increases the ramp angle with which the second lobes 34 ride. In general, the magnitude of the torque limit threshold can be increased by increasing the amount of friction between the sleeve 26 and the coupler socket 30. Conversely, the magnitude of the torque limit threshold can be reduced by decreasing the friction between the sleeve 26 and the coupler socket 30. For example, the gap 172 between the second lobe 34 of the coupler 24 and the first groove 36 of the sleeve 26 can be decreased to increase surface friction while increasing the gap 172 typically decreases surface friction which generally results in a decrease in the magnitude of the torque limit.

Furthermore, the torque threshold limit may also be adjusted by constructing the torque limiting mechanism 16 of different materials having different modulus of elasticity. For example, constructing the torque limiting mechanism 16 from materials having a greater modulus of elasticity generally increases the magnitude of the torque limit. In contrast, constructing the torque limiting mechanism 16 from materials having a lesser modulus of elasticity, generally decreases the torque threshold limit. Non-limiting examples of materials that have a relatively "low" modulus of elasticity may include, but are not limited to, rubber and low density polyethylene having modulus of elasticity's ranging from about 0.01 GPa to about 1.0 GPa. Non-limiting examples of materials having a relatively "medium" modulus of elasticity may include, but are not limited to, polypropylene, polyethylene terephthalate (PET), nylon and polystyrene having a modulus of elasticity ranging from about 1.0 GPa to about 4.0 GPa. Non-limiting examples of relatively "high" modulus of elasticity generally comprise those materials having a modulus of elasticity greater than 4.0 GPa. As defined herein modulus of elasticity is a mechanical property of linear elastic solid materials. Modulus of elasticity is the force (per unit area) that is required to stretch (or compress) a material sample. In a preferred embodiment, the torque limiting tool can be design to apply a maximum torque from about 0.007 N-m (1 oz. per in) to about 122 N-m (90 lbf).

In a preferred embodiment the housing 18 may be composed of a polymeric material. In addition, the sleeve 26 and/or coupler 24 may be composed of a polymeric material. Such materials may include but are not limited to thermoplastics such as acrylics, acrylonitrile butadiene styrene (ABS), poly(hexamethylene adipamide), polylactic acid, polybenzimidazole, polycarbonate, polyether sulfone, poly ether ether ketone (PEEK), polyetherimide, polyethylene, polyphenylene oxide, polyphenylene sulfide, polypropylene, polystyrene, polyvinyl chloride, and combinations thereof. Such polymeric materials provide a durable structure and allow for flexure of the first and second lobes 32, 34 and/or first and second grooves 36, 38. Alternatively, the housing 18 and/or the sleeve 26 and coupler 24 may be constructed of a metallic material such as various stainless steel alloys, a ceramic material, such as a stainless steel alloy, or combinations thereof.

While the preferred embodiments of the torque limiting tool and methods have been described in reference to the environment in which they were developed, they are merely illustrative of the principles of the inventions. Other embodiments and configurations may be devised without departing from the spirit of the inventions and the scope of the appended claims.

What is claimed is:

1. A torque limiting tool, comprising:
   a) a housing having spaced proximal and distal housing portions that extend along a rotational axis;
   b) a torque limiting mechanism disposed within the housing, the torque limiting mechanism comprising:
      i) a sleeve having a sleeve annular sidewall that defines a sleeve throughbore extending therethrough from a sleeve proximal end to a sleeve distal end along the rotational axis, at least one first lobe formed by the annular sidewall outwardly projecting from the annular sidewall away from the rotational axis and at least one first groove at least partially formed within the sleeve sidewall positioned adjacent to the first lobe, wherein:
         both the first lobe and the first groove extend lengthwise along the sleeve sidewall; and
         the first lobe comprises a base lobe positioned proximate the rotational axis that extends to a first lobe plateau having a first lobe plateau surface positioned distal the rotational axis, wherein the first lobe plateau surface is curved;
      ii) a coupler having a coupler proximal portion that extends to a coupler distal portion, a socket dimensioned to receive the sleeve formed within the coupler distal portion by a coupler annular sidewall, the socket having a socket interior that extends longitudinally from a socket opening at the coupler distal end part way towards the proximal coupler end, wherein at least two second lobes outwardly project from the coupler annular sidewall of the socket towards the socket interior and the at least one second groove is at least partially formed within the annular coupler sidewall positioned between the two second lobes; and
   c) wherein the sleeve is positioned within coupler socket so that the sleeve first lobe is received within the socket second groove and the socket second lobe is received within the first sleeve groove and wherein application of a torque at the proximal coupler portion causes the coupler socket to engage with the sleeve thereby causing the sleeve to rotate about the rotational axis.

2. The torque limiting tool of claim 1 wherein the sleeve comprises three spaced apart first lobes that are circumferentially positioned about the sleeve annular sidewall.

3. The torque limiting tool of claim 1, wherein the first lobe plateau surface is tangent to an imaginary circle having an origin at the rotational axis.

4. The torque limiting tool of claim 1 wherein the first groove comprises respective left and right groove sidewall surfaces that outwardly extend from a groove base surface proximate the rotational axis, wherein the groove left sidewall surface defines a right sidewall surface of the first lobe and the groove right sidewall surface defines a left sidewall surface of an adjacent first lobe.

5. The torque limiting tool of claim 4 wherein the first groove base surface has a convex curvature with respect to the rotational axis.

6. The torque limiting tool of claim 4 wherein the left and right first groove sidewall surfaces are curved.

7. The torque limiting tool of claim 1 wherein the first groove comprises respective left and right groove sidewall surfaces extending from a first groove base surface proximate the rotational axis, wherein the left groove sidewall surface has a first transition surface that extends from the groove base surface to a first transition point positioned along the left sidewall surface between the base surface and the first lobe plateau surface distal the rotational axis and a second transition surface that extends between the first transition point and the first lobe plateau surface, wherein the first transition surface comprises a convex curvature and the second transition surface comprises a concave curvature with respect to the rotational axis.

8. The torque limiting tool of claim 7 wherein the first groove base surface has a first radius of curvature, the first transition surface has a second radius of curvature and the second transition surface has a third radius of curvature, wherein the first, second and third radius of curvatures are different.

9. The torque limiting tool of claim 1 wherein the first lobe extends from a first lobe distal end at the sleeve distal end to a first lobe proximal end positioned distal of the sleeve proximal end.

10. The torque limiting tool of claim 1 wherein a sleeve end wall is positioned at the sleeve distal end, wherein the sleeve end wall radially extends from the sleeve annular sidewall.

11. The torque limiting tool of claim 1 wherein the coupler comprises three, spaced apart second lobes circumferentially positioned about the coupler annular sidewall, each projecting towards the socket interior.

12. The torque limiting tool of claim 1 wherein the second lobe comprises a second lobe base positioned distal the rotational axis that extends to a second lobe plateau having a second lobe plateau surface positioned proximate the rotational axis, wherein the second lobe plateau surface is curved.

13. The torque limiting tool of claim 12 wherein the second lobe plateau surface is tangent to an imaginary circle having an origin at the rotational axis.

14. The torque limiting tool of claim 1 wherein the annular coupler sidewall has a uniform thickness about a circumference of the coupler socket.

15. The torque limiting tool of claim 1 wherein the proximal coupler portion comprises a driver end having a keyed interface.

16. The torque limiting tool of claim 15 wherein the keyed interface comprises a cross-section oriented perpendicular to the rotational axis having a polygon shape.

17. The torque limiting tool of claim 1 wherein the sleeve or the coupler are composed of a polymeric material or a metallic material.

18. The torque limiting tool of claim 1 wherein the sleeve or the coupler is composed of a material having a modulus of elasticity ranging from about 0.01 GPa to about 10 GPa.

19. The torque limiting tool of claim 1 wherein the first lobe of the sleeve has a first lobe width oriented about perpendicular to the rotational axis and the second lobe of the coupler socket has a second lobe width oriented about perpendicular to the rotational axis, wherein the second lobe width is less than the first lobe width.

20. The torque limiting tool of claim 1 wherein a first gap extends between a plateau surface of the second lobe positioned distal the rotational axis and a base surface of the first groove positioned proximate the rotational axis.

21. The torque limiting tool of claim 1 wherein a second gap extends between a base surface of the second groove positioned distal the rotational axis and the first lobe plateau.

22. The torque limiting tool of claim 1 wherein the housing comprises a first housing section and a second housing section that join together, wherein the first and second housing sections are identical.

23. A torque limiting tool, comprising:
a) a housing having spaced proximal and distal housing portions that extend along a rotational axis;
b) a torque limiting mechanism disposed within the housing, the torque limiting mechanism comprising:
i) a sleeve having a sleeve annular sidewall that defines a sleeve throughbore extending therethrough from a sleeve proximal end to a sleeve distal end along the rotational axis, at least one first lobe formed by the annular sidewall outwardly projecting from the annular sidewall away from the rotational axis and at least one first groove at least partially formed within the sleeve sidewall positioned adjacent to the first lobe, wherein: both the first lobe and the first groove extend lengthwise along the sleeve sidewall;
ii) a coupler having a coupler proximal portion that extends to a coupler distal portion, a socket dimensioned to receive the sleeve formed within the coupler distal portion by a coupler annular sidewall, the socket having a socket interior that extends longitudinally from a socket opening at the coupler distal end part way towards the proximal coupler end, wherein at least two second lobes outwardly project from the coupler annular sidewall of the socket towards the socket interior and the at least one second groove is at least partially formed within the annular coupler sidewall positioned between the two second lobes;
c) wherein the sleeve is positioned within coupler socket so that the sleeve first lobe is received within the socket second groove and the socket second lobe is received within the first sleeve groove and wherein application of a torque at the proximal coupler portion causes the coupler socket to engage with the sleeve thereby causing the sleeve to rotate about the rotational axis; and
(d) wherein the sleeve or the coupler comprises material having a modulus of elasticity ranging from 0.01 GPa to 10 GPa.

* * * * *